United States Patent [19]

Lopez et al.

[11] Patent Number: 4,600,004

[45] Date of Patent: Jul. 15, 1986

[54] INTRAOCULAR LENS HOLDER AND INSERTER

[76] Inventors: Osvaldo Lopez, 11 N. Wabash, Chicago, Ill. 60602; Gerald Horn, 5415 W. Sheridan Rd., Chicago, Ill. 60640

[21] Appl. No.: 415,805

[22] Filed: Sep. 8, 1982

[51] Int. Cl.⁴ .......................... A61B 17/00; A61F 2/16
[52] U.S. Cl. ...................................... 128/303 R; 623/6
[58] Field of Search .............. 3/13; 128/303 R; 623/6

[56] References Cited

U.S. PATENT DOCUMENTS 4,251,887 2/1981 Anis .......................................... 3/13

Primary Examiner—Ronald L. Frinks
Attorney, Agent, or Firm—Kane, Dalsimer, Kane, Sullivan and Kurucz

[57] ABSTRACT

An apparatus for storing an intraocular lens and inserting it into an eye having elongated tubular member with a flared end, and side walls for closing the haptics of lens around the lens. The lens is stored in the flared end and after the narrow end is inserted into the eye through an appropriate opening, the lens is made to slide through the member into the eye.

7 Claims, 8 Drawing Figures

INTRAOCULAR LENS HOLDER AND INSERTER

BACKGROUND OF THE INVENTION

This invention pertains to an apparatus for holding an intraocular lens for inserting an intraocular lens into the eye.

Various diseases of the human eye may require removal of the eye's natural lens. For example, one of these diseases causes the natural lens to become opaque, thus blocking the light before it hits the retina. This effect is commonly referred to as a cataract.

After the lens has been removed, an artificial lens must be provided to restore the patient's vision. Generally there are three methods of providing such a lens: regular glasses, external contact lens and intraocular lens.

Regular glasses used for cataracts are very thick and therefore found aesthetically objectionable by many patients. Contact lenses are inappropriate to some patients, especially older ones who do not have the dexterity necessary for inserting or removing the lens. Thus, for many patients the intraocular lenses present the best alternative.

Depending on their actual position within the eye, intraocular lenses are categorized either as anterior chamber lenses or posterior chamber lenses. As the name implies an anterior chamber lens is installed in the anterior chamber between the iris and the ocular jelly. Sometimes, this lens is positioned in the plane of the iris. In order to insure that the lens does not shift, the lens is sometimes sutured or otherwise affixed to the iris. Anterior chamber lenses are the predominant and safer type of lenses, and of course they must be used after intracapsular surgery, during which the capsular bag is removed.

Posterior chamber lenses can be used after extracapsular surgery, i.e., when the cataract is removed but the capsular bag is left in place. Although posterior chamber lenses may be positioned between the bag and the iris, it was found that it is safer to install these lenses within the capsular bag itself.

Intraocular lenses have gone through an evolution of their own. While the initial lenses had bulky, complicated appendages for securing the lens within the eye, the latest lenses have much simpler mechanisms. One of the most common type of intraocular lens have a number a flexible loops or haptics. In the relaxed position these loops are coplanar with the lens and engage the side walls of the eye in a spring action thus holding the lens in place. The loops are made of polypropylene or other similar material and lenses are available with loops of a variety of sizes, shapes, and colors.

It is well known that eye surgery is a very delicate procedure. Any inadvertant move on the part of the surgeon may further damage the eye. This is especially true for the process of implanting an intraocular eye because the lens itself is very small and, further, it must be precisely positioned so that it can focus the light entering the eye onto the retina. The lenses with loops are especially difficult to install because the loops in their open position cover an area which is much larger than the actual area of the lens. Various devices have been made which assist the surgeon in this procedure, however most of them are too bulky and expensive.

One device which has been used in particular with lenses having loops is the so-called SHEET GLIDE. This device is simply a flat flexible plastic strip which is slightly narrower than the diameter of the lens. In order to use this device, the surgeon makes an appropriate incision in the eye, and then he slips the SHEET GLIDE into the eye with its tip positioned in the general location to be occupied by the lens. Next, he slides the lens on the glide into the eye. The incision in the eye must be large enough to accomodate the loops, and the SHEET GLIDE does not provide any protection of the eye during the implantation.

OBJECTIVES AND SUMMARY OF THE INVENTION

Therefore, it is the objective of this invention to provide an apparatus for inserting an intraocular lens in the eye which protects the eye during insertion.

Another objective is to provide an apparatus which requires a smaller opening then previously disclosed, thus making the operation safer.

A further objective is to provide an apparatus which keeps the loops close to the lens while the lens is being positioned within the eye.

Yet another objective is to provide an apparatus which can hold the lens for storage prior to its use, and from which the lens can be inserted directly without the necessity of removing the lens from a case.

Other objectives and advantages of the invention shall be described in the following description.

In accordance with the invention there is provided an apparatus for inserting an intraocular lens with loops or haptics, comprising a flat elongated tubular member with the lens being affixed at one end.

After an incision is made in the eye, the other end of the member is inserted through the incision and extended to the desired location of the lens. The lens then is made to slide through the member until it reaches the desired position. Two side walls of the member engage the haptics, and force the loop in a closed position around the lens while it slides through said member.

DESCRIPTION OF THE PREFERRED EMBODIMENT

A preferred embodiment of the invention shall now be described in relation to a posterior chamber lens. It must be understood however that the device would work equally well with an anterior chamber lens.

Referring to FIGS. 1-6, a typical intraocular lens 10 comprises a lenticular body which is made out of a transparent material and has the required optical characteristics necessary to correct the patient's vision. A number of holes such as 30 are provided within the body to allow the surgeon to manipulate the lens. Imbedded in the body are two haptics or loops 40 and 50. These loops are flexible, have a curvilinear shape in their relaxed or open position, and may be wrapped around the circumference of the body 20. This later position shall be called the closed position.

Figure 1:
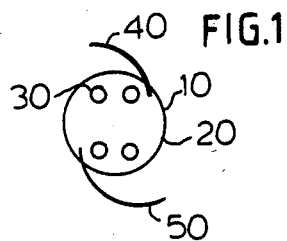
FIG. 1 shows a typical intraocular lens having haptics.
Figure 2:
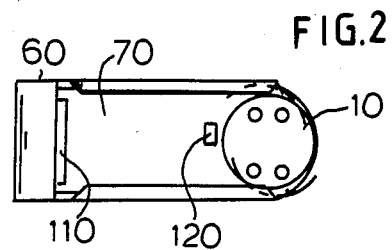
FIG. 2 is a plan view of the invention.
Figure 4:
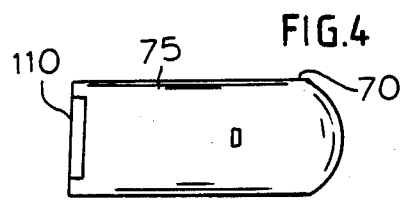
FIG. 4 is a first end view of the invention.
Figure 5:
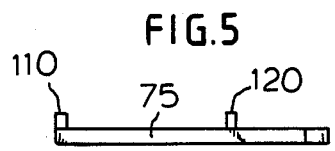
FIG. 5 is a second end view of the invention; and different positions of the lens
Figure 3:
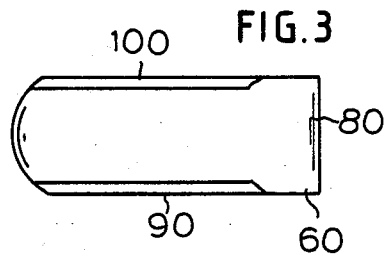
FIG. 3 is a plan view of the bottom part of the invention.
Figure 6:
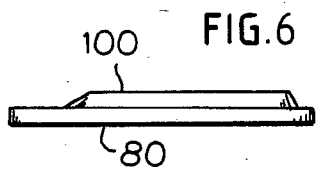
FIG. 6 shows the different positions of the lens as it slides through the apparatus.
Figure 7:
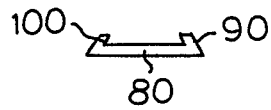
Figure 8:
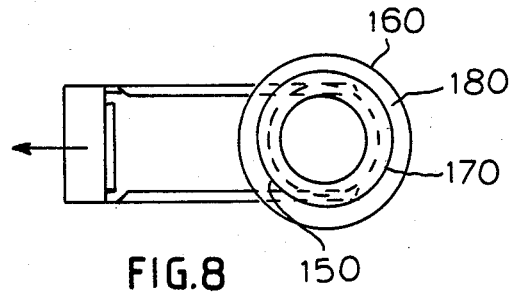

The apparatus comprises a top part 60, sides 70 and 80, and bottom part 90. These four elements form an elongated flat tube which is shown as having a rectangular cross-section (FIGS. 4 and 5). It is to be understood that the invention is not limited to this shape. Preferrably the apparatus has the following dimensions:
overall length = 16 mm
thickness of the top part =0.05–0.07.5 mm (2–3 mils)
thickness of the bottom =0.015 mm (0.6 mils)
normal width =7.0–7.25 mm At one end 100, for a distance of about 5 mm, the apparatus is flared out to a maximum width of about 8.5 mm.

At end 100, bottom part 90 is shorter than top part 60 to create a 1–2 mm overhang. The flared part is the storage portion of the lens, where the lens is held by the apparatus during storage. For this purpose the lens is oriented with two of its holes 30 are close to end 100, thus allowing the lens to be affixed to the overhang by a suture or similar means.

At the second, open end 110, the top part forms a second overhang of about 4 mm which is provided to protect the eye while the lens is disengaging from the apparatus.

An incision 150 is made in eye 160 between the corner 170 amd the choroidal tissues 180. The incision 150 need not be wider than the width of the apparatus. End 110 is next extended into the capsular bag 190 until it reaches the desired postion. Next, the lens is freed (if necessary) from the first overhang and rotated about 45° until the haptics are fixed in the closed position as they are engaged by the side walls 70 and 80. This step is performed by the use of a spatula normally used during such surgical procedures. After the haptics have been forced into the closed position, the lens is made to slide through the apparatus with the spatula into the eye. At end 110 the lens comes out of the apparatus and the haptics open up to engage the sides of the eye. The apparatus is then removed from the eye.

One skilled in the art will appreciate the fact that during insertion, the haptics are held closed, and therefore, the risk of injuring the eye is reduced. The apparatus also protects both the anterior and the posterior sides of the capsular bag while the lens is being inserted. This facet of the invention becomes very important when the invention is used for an anterior chamber lens. As it was previously shown, the anterior chamber lens is installed above the iris, and above the ocular jelly contained in the anterior chamber. During any surgical operation, contact with this jelly must be avoided as much as possible. If the present invention is used to insert the lens, the jelly is protected by the apparatus.

The apparatus may be made of any of the common plastics in use today. Since it is very inexpensive to manufacture, it may be disposed after a single use, thus saving the sanitizing costs.

In summary, the present invention provides an inexpensive apparatus for storing and inserting an intraocular lens in an eye by keeping the haptics closed until after the lens has been positioned, and without the use of awkward and bulky instruments. Furthermore the lens can be stored safely in the apparatus at the place of manufacture and need not be removed before its insertion.

I claim:

1. An apparatus for storing an intraocular lens with haptics for inserting it into an eye comprising an elongated tubular member with a first end for storing said lens said first end having flared sidewalls to engage said haptics when said lens is inserted into the eye and force them around said lens and second end which is open, whereby the lens is inserted by inserting said second end through an incision in the eye, then sliding said lens through said member into the eye and removing said second end from said eye.

2. the apparatus of claim 1 wherein said member is formed by a top part, a bottom part and two sides, said top part being longer than said bottom part to form a first overhand at said first end to which said lens is affixed.

3. The apparatus of claim 2 wherein said top is longer than said bottom to form a second overhang at said second end provided to protect the eye while the lens exits from said member.

4. An apparatus for storing an intraocular lens and inserting it into an eye comprising
a top part;
a bottom part; and
two sides;
said top part, bottom part, and two sides forming an elongated tubular member with a first end and a second end said top part extending beyond said bottom part to provide a protective overhang;
said member having a length of 16 mm;
said member having a width of 7–7.25 mm;
whereby said lens is inserted by making an incision in the eye, inserting said second end into the eye until said overhang is disposed at a preselected position, sliding said lens through said tubular member and releasing said lens at said preselected position.

5. The apparatus of claim 4 wherein said first end is flared out and has a width of 8.5 mm.

6. The apparatus of claim 4 wherein said bottom is shorter than said top at said first end by 1–2 mm.

7. The apparatus of claim 4 wherein said bottom is shorter than said top at said second end by 4 mm.

* * * * *